(12) United States Patent
Yoshimine

(10) Patent No.: US 7,636,445 B2
(45) Date of Patent: Dec. 22, 2009

(54) STETHOSCOPE APPARATUS

(76) Inventor: Takashi Yoshimine, 5-3-107, Minami-cho, Toda-shi, Saitama, 335-0025 (JP)

( * ) Notice: Subject to any disclaimer, the term of this patent is extended or adjusted under 35 U.S.C. 154(b) by 220 days.

(21) Appl. No.: 10/570,767

(22) PCT Filed: May 18, 2005

(86) PCT No.: PCT/JP2005/009042

§ 371 (c)(1), (2), (4) Date: Mar. 7, 2006

(87) PCT Pub. No.: WO2006/123407

PCT Pub. Date: Nov. 23, 2006

(65) Prior Publication Data

US 2007/0058818 A1    Mar. 15, 2007

(51) Int. Cl.
A61B 7/04 (2006.01)
A61B 7/02 (2006.01)

(52) U.S. Cl. .................... 381/67; 181/131
(58) Field of Classification Search .............. 381/79, 381/311, 334, 67; 181/131
See application file for complete search history.

(56) References Cited

U.S. PATENT DOCUMENTS 6,279,677 B1 * 8/2001 Sanchez-Zambrano ...... 181/131
2001/0030077 A1 * 10/2001 Watson ........................ 181/131
2003/0002685 A1 * 1/2003 Werblud ........................ 381/67
2004/0151077 A1 * 8/2004 McKay ......................... 368/278

FOREIGN PATENT DOCUMENTS

| EP | 1 495 721 A2 | 1/2005 |
| JP | 57-160442 A | 10/1982 |
| JP | 60-261439 A | 12/1985 |
| JP | 09-000518 A | 7/1997 |
| JP | 2005-27751 A | 2/2005 |
| JP | 2005-052521 A | 3/2005 |
| KR | 2003-0080714 A | 10/2003 |

OTHER PUBLICATIONS

Korean Office Action, 620030356387 (5 pages) with Japanese Translation (5 pages).

* cited by examiner

Primary Examiner—Vivian Chin
Assistant Examiner—George C Monikang
(74) Attorney, Agent, or Firm—Rader, Fishman & Grauer, PLLC

(57) ABSTRACT

To provide a stethoscope apparatus that can contribute to medical cares that can eliminate anxieties of a patient as much as possible.

A stethoscope apparatus 10 according to the embodiment integrally mounts a speaker 9 and a microphone 8; accordingly, the speaker 9 can reproduce sounds obtained with the microphone 8. For instance, when a physician explains the pathology and so on to a patient with the patient allowed hearing sounds from a speaker, the patient can be diagnosed at ease more than ever.

8 Claims, 13 Drawing Sheets

FIG. 12
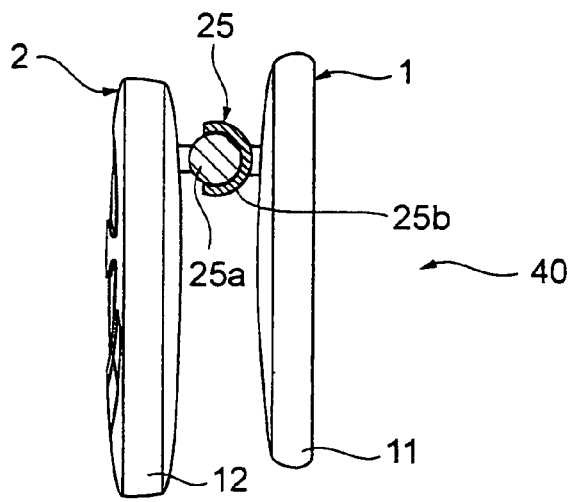
FIG.12A
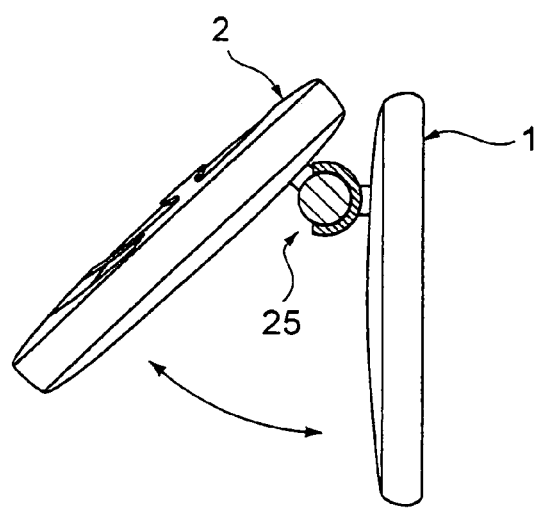
FIG.12B
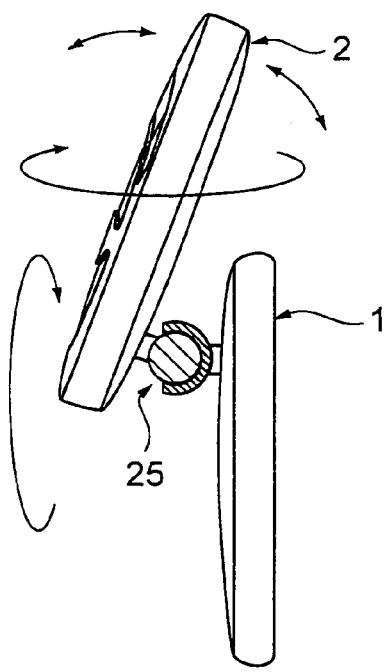
FIG.12C

STETHOSCOPE APPARATUS

FIELD OF THE INVENTION

The present invention relates to a stethoscope apparatus that is used for medical practices.

BACKGROUND OF THE INVENTION

In medical practices, a physician frequently employs a stethoscope for diagnosing patients. Owing to the diagnosis with a stethoscope, from biological sounds of patients such as vesicular breath sounds, bronchial breath sounds, low tone continuous sounds, squawks and bubbling rales, various pathologies can be grasped. Owing to the biological sounds from a stethoscope, not only pathologies of a heart and a respiratory system, but also various pathologies of other organ and bowel can be grasped.

Recently, there is a stethoscope in which biological sounds are electrically converted and amplified, followed by outputting with a speaker or the like (Published Application in JP: JP-A No. 2005-52521 (paragraph No. [0011] and FIG. 1).

DISCLOSURE OF INVENTION

Problems to be Solved

In recent years, in medical practices, an idea called an informed consent where a physician explains pathology, a method of treatment and advantages and risks of the treatment to a patient and thereby obtains patient's consent of the treatment becomes important. However, since the medical cares are specialized, in some cases, patients cannot sufficiently understand an explanation of the physician. As a result, there are cases where the patients conceive anxiety of their own pathologies.

Means for Solving the Problem

In view of the above circumstances, the invention intends to provide a stethoscope apparatus that contributes to a medical care that can eliminate patient's anxiety as much as possible.

In order to achieve the above object, the stethoscope apparatus according to the invention, comprising: a microphone, a speaker that outputs a sound in accordance with an electrical signal generated by the microphone, and a housing that integrally mounts the microphone and speaker.

According to the invention, the microphone and the speaker are integrally mounted on the housing and the speaker can reproduce sounds obtained by the microphone. For instance, when a physician explains the pathology and so on to a patient with the patient allowing hearing sounds from the speaker, the patient can be diagnosed at ease more than ever.

In the invention, the stethoscope apparatus may further comprise a diaphragm capable of vibrating supported by the housing.

In the invention, the housing has a first housing on which the microphone is mounted, a second housing on which the speaker is mounted, and a adjusting mechanism capable of adjusting an angle of the second housing to the first housing. Thereby, a direction in which the sounds from the speaker are outputted can be appropriately adjusted. For instance, the physician can appropriately adjust a direction so that the physician or the patient may easily hear the sounds from the speaker. The angle of the second housing to the first housing means angles in various planes and is not restricted to an angle only in one plane.

For instance, when the adjusting mechanism has a uniaxial hinge mechanism, the angle of the second housing to the first housing can be adjusted in one plane.

In the invention, the first housing has a contact portion that is brought into contact with a patient, and the contact portion and the speaker, respectively, are disposed to the first and second housings so that the speaker outputs the sound to an opposite side of the contact portion when the first and second housings are closed with the hinge mechanism. Thereby, a physician who faces a patient can listen to the patient with a stethoscope apparatus in a state where sounds from the speaker of the stethoscope apparatus can be easily heard. Furthermore, the physician can listen to the patient with the first and second housings closed, that is, with the stethoscope apparatus rendered relatively compact.

In the invention, the adjusting mechanism is a universal joint. Therewith, the physician can adjust the second housing to the first housing in all angle directions.

In the invention, the stethoscope apparatus further comprises a sensor that is disposed to the housing and can detect when the stethoscope apparatus comes into contact with the patient; and a power supply of which electric power is inputted in accordance with a signal detected by the sensor. Thereby, the power saving can be realized. For instance, when the power supply of the stethoscope apparatus is a battery type, being particularly demanded to save power, the invention is particularly effective. Furthermore, since the power is not inputted until the stethoscope apparatus comes into contact with the patient, the stethoscope apparatus does not pick up noises and so on before the stethoscope apparatus comes into contact with the patient.

In the invention, the stethoscope apparatus further comprising a memory portion that memorizes a sound obtained by the microphone, and a memory controller that controls the memory operation. The stethoscope apparatus may still further comprise a function of reproducing sounds memorized by the memory portion with the speaker. The memory portion is convenient when it is one that memorizes digital data. However, without necessarily restricting to the digital data, the memory portion may be one that memorizes analog data. The memory portion may be one incorporated in the stethoscope apparatus or may be a portable memory as shown below.

In the invention, the stethoscope apparatus includes a slot where a portable recording medium can be loaded in the housing. The stethoscope apparatus further includes an interface that, in a state where the recording medium is loaded in the slot, can transmit sound data obtained by the microphone to the recording medium; and a controller that controls at least one of recording the data on the recording medium through the interface and reproducing data recorded on the recording medium through the interface. In this case, the data recorded on the portable recording medium are conveniently digital data. Thereby, data of biological sounds can be copied on a computer and a physician can analyze the biological sounds with a computer in more detail.

In the invention, the stethoscope apparatus further comprising a clip mechanism disposed to the housing. So far, a stethoscope is provided with an auditory tube; accordingly, a physician, when hooking the auditory tube on a neck of the physician, can carry the stethoscope without using a hand. In the invention, such an auditory tube and other cables are not included. Accordingly, a physician can conveniently carry the stethoscope apparatus with it clipped with such a clip mechanism to a pocket of a physician's cloth.

In the invention, the clip mechanism has a plane table-shaped or frame-shaped pressure member. When a shape of the housing that has the speaker and so on is considered, the plane table-shaped or frame-shaped pressure member can stabilize a clipped state.

In the invention, the stethoscope apparatus further comprising storing means for storing data of patterns of a plurality of biological sounds, and pattern-matching means for pattern-matching a biological sound obtained from a patient with the microphone with the respective pattern data storing with the storing means. When a diagnosis due to the pattern matching is utilized, a physician, being inhibited from misdiagnosing, can effectively diagnose. On the other hand, the diagnosis with the pattern matching can be used also complementarily in the physician's diagnosis.

In the invention, the storing means store a plurality of informations on pathology so that each of the information corresponds to the respective pattern data. The stethoscope apparatus further comprising pathology output means for outputting information of the pathology corresponding to at least one pattern data matched by the pattern-matching means is extracted from the storing means and outputted through the speaker. Alternatively, the stethoscope apparatus may further comprising, display means; and display control means that control so that information of the pathology corresponding to at least one pattern data matched by the pattern-matching means is extracted from the storing means and displayed through the display means. Thereby, the patient can know the pathologies from both the physician and the stethoscope apparatus and can be diagnosed at more ease.

EFFECTS OF THE INVENTION

As mentioned above, according to the invention, the medical care that can eliminate the patient's unease and is due to more satisfied informed consent can be realized.

BEST MODE FOR CARRYING OUT THE INVENTION

In what follows, embodiments according to the invention will be described with reference to the drawings.

FIG. 1 is a perspective view showing a stethoscope apparatus involving a first embodiment according to the invention. The stethoscope apparatus 10 includes a diaphragm portion 1 and a speaker portion 2.

FIG. 2 is a diagram seen from a diaphragm portion 1 side of the stethoscope apparatus 10 shown in FIG. 1. FIG. 3 is an exploded perspective view showing the diaphragm portion 1, and FIG. 4 is an exploded perspective view showing the speaker portion 2. Furthermore, FIG. 5 is a side view showing the stethoscope apparatus 10.

As shown in FIG. 3, the diaphragm portion 1 includes a housing 11. The diaphragm 6 is vibratably mounted to an opening 11a disposed to the housing 11. A biological sound of, for instance, a patient obtained owing to a vibration of the diaphragm 6 is constituted so as to be collected with a sound collecting plate 7, and the sound collecting plate 7 is disposed so as to be supported with a supporter 13 fixed to for instance the housing 11. Since the diaphragm 6 is a vibrating member, the diaphragm 6 and the sound collecting plate 7 are disposed so as not to come into contact with each other.

At a substantial center of the sound collecting plate 7, a hole-like sound passage 7a is disposed to allow sounds due to the vibration of the diaphragm 6 to pass and a microphone 8 is disposed to the sound passage 7a. Thereby, the microphone 8 converts sounds collected by the sound collecting plate 7 into electrical signals. For the microphone 8, when it is required to be for instance a smaller size, an electrostatic type or a piezoelectric type is used. However, without restricting thereto, it may be an electromagnetic type like a speaker.

As shown in FIG. 4, the speaker portion 2 is constituted with a circuit board 17 and a speaker body 9 (hereinafter, simply referred to as a speaker 9) incorporated in the housing 12 and with a cover 19 loaded to the opening 12a of the housing 12. The speaker 9 may have a general structure where a conical vibrating plate 9a is attached to a frame 9b. A planar shape of the speaker 9 may not be a circular one such as exemplified but may be for instance an elliptical one or an oval one. On the circuit board 17, electronic components such as an IC22 and a capacitor are mounted. The speaker 9 is electrically connected to the electronic components such as the ICs of the circuit board 17 through a not shown cable or the like.

On a front surface of the cover 19, an operation input portion 4 is disposed to carry out recording or reproduction of sounds obtained by the microphone. When the operation input portion 4 is touched with for instance a human finger, a not shown contact point disposed to the operation input portion 4 comes into contact with an electrode 21 of the circuit board 17 to trigger an operation such as the reproduction. A power switch may be disposed to the operation input portion 4 or to a separate position. To a surface of the cover 19, a speaker cover 3 provided with a plurality of holes is attached.

With reference to FIG. 3, an electric cable and so on of the microphone 8 are wired through a hole 13a opened in the support 13 and a hole 12b opened in the housing 12 to the circuit board 17. As shown in FIG. 5, for instance, the diaphragm portion 1 and the speaker portion 2 are connected with a uniaxial hinge mechanism 5. As shown in FIG. 6, by use of the hinge mechanism 5, for instance, with a shaft 5a as a rotation axis, an angle of the speaker portion 2 can be appropriately varied to the diaphragm portion 1 to fix positions of both at a desired angle. With the hinge mechanism 5, the diaphragm portion 1 and the speaker portion 2 can be constituted so as to open at an angle less than 180° or more than 180° at maximum. The electrical cables and so on of the microphone 8 are wired for instance inside of a shaft 5a of the hinge mechanism 5 and connected to the circuit board 17 of the speaker portion 2.

The housings 11 and 12 or the diaphragm 6 are constituted of for instance a resin. However, without restricting to such a material, the housing 11 may be formed of metal or other materials. The housing 11 and the support 13 can be integrally molded; however, these may be formed from separate members respectively followed by connecting. The speaker cover 3 is formed also of a resin or metal.

Though not shown in the drawing, a power supply of the stethoscope apparatus 10 can be constituted into for instance a rechargeable or exchangeable battery type. In the case of the rechargeable type, on the circuit board 17, an electrode or the like electrically connected to a rechargeable battery is disposed and the electrode may be exposed from the housing 12. Alternatively, without disposing such an electrode, a non-contact rechargeable battery may be adopted. On the other hand, in the case of the exchangeable battery, when a generally used coin battery is used, the stethoscope apparatus 10 can be miniaturized or thinned.

FIG. 7 is a block diagram showing an electrical configuration of the stethoscope apparatus 10. The stethoscope apparatus 10 includes a CPU (Central Processing Unit) 31, a recording/reproducing controller 32, a memory 33 and a power supply 34.

The CPU 31 collectively and totally controls an operation of the stethoscope apparatus 10. The recording/reproducing controller 32, based on an operation input portion instruction from the operation input portion 4, controls an operation of recording or reproduction. In particular, the recording/reproducing controller 32 converts sounds that are analog inputted from the microphone 8, for instance at an appropriate sampling frequency, into digital data at a quantized bit number of 4 bits, 8 bits or more. The recording/reproducing controller 32 may compress the data being recorded. The memory 33 memorizes for instance digital data of the sound. As the memory 33, a flash memory is used; however, a recording medium other than this, for instance, a magnetic disc such as a hard disc may be used.

A signal that drives the speaker 9 may be an analog signal; however, based on data digitalized as shown above, a speaker output may be controlled. The electrical signal from the microphone 8 is preferably passed through a not shown amplifier or noise filter.

When a physician diagnoses a patient with the stethoscope apparatus 10, the physician holds the housing 11 of the diaphragm portion 1 and, while bringing a diaphragm 6 into contact with the patient, listens to biological sounds of the patient generated from the speaker portion 2. In this case, since the stethoscope apparatus 10 is provided with the hinge mechanism 5, an angle of the speaker portion 2 can be varied so that the physician may easily listen to sounds. In particular, as shown in FIG. 5, in a state where the diaphragm portion 1 and the speaker portion 2 are closed and the diaphragm 6 is brought into contact with a skin of the patient, a direction in which sounds are outputted from the speaker portion 2 is constituted so as to be opposite to a side on which the diaphragm 6 is disposed. That is, when, with the first and second housings closed to make the stethoscope apparatus compact, a physician faces a patient and diagnoses with the stethoscope apparatus 10, a state where the physician can easily listen to speaker sounds results.

Furthermore, the housing 11 has a vibration plate 6 as a contact portion that is brought into contact with a patient. As shown in FIG. 5, in a state where the stethoscope apparatus 10 is closed, the biological sounds are outputted from a speaker 9 toward a side opposite to the vibration plate 6. Thereby, the physician who faces the patient can listen to speaker sounds of the stethoscope apparatus 10 in an easily audible state. Furthermore, in that case, the physician can, with the stethoscope apparatus 10 closed as shown in FIG. 5, that is, with the stethoscope apparatus 10 rendered relatively compact, listen to the patient with the stethoscope apparatus 10.

Still furthermore, the physician can operate the operation input portion 4 at the time of auscultation to record sounds on the memory 33 and reproduce the recorded sounds later. A volume can be preferably controlled.

As mentioned above, since the stethoscope apparatus 10 according to the embodiment integrally mounts the microphone 8 and the speaker 9, sounds obtained with the microphone 8 can be reproduced by use of the speaker 9. For instance, the physician, while allowing the patient to listen to the sounds from the speaker portion 2, can diagnose the patient and explain the pathologies to the patient. Accordingly, the patient can be diagnosed at more ease than ever.

When the physician listens to the patient with a stethoscope in a state shown in FIG. 5, an output direction of sounds of the speaker portion 2 is in a direction opposite to the patient; however, the patient can easily listen to the sounds of the speaker portion 2. When the patient is difficult to listen to the sounds, in order to make easy to listen to, the physician may appropriately vary an angle of the speaker portion 2. Alternatively, for instance, when the diaphragm portion 1 and the speaker portion 2 are opened so as to be substantially vertical to each other (so that an output plane of the speaker sounds and a vibration direction of the diaphragm 6 may be substantially in parallel with each other), with the diaphragm portion 1 brought into contact with the patient, an output direction of the speaker portion 2 can be directed upward. Thereby, both the patient and physician can easily listen to the speaker sounds.

FIG. 8 is a perspective view showing a stethoscope apparatus involving another embodiment of the invention. FIG. 9 is a block configuration diagram of the stethoscope apparatus. In the descriptions after this, of the members and functions of the stethoscope apparatus 10 according to the above-mentioned embodiment, similar ones will be simplified in or omitted from describing and different points therefrom will be mainly described. As shown in FIG. 8, the stethoscope apparatus 20 includes a slot 12c to which a portable external memory 41 is detachably attached. As the portable external memory 41, for instance, a semiconductor memory such as a flash memory can be cited. With reference to FIG. 9, the stethoscope apparatus 20 includes an interface 36 accessible to the external memory 41. Thereby, with the portable external memory 41 loaded in the slot 12c, data of sounds obtained by the microphone 8 can be communicated to the memory 41. In this case, the recording/reproducing controller 32 controls a recording or reproducing operation to the memory 41.

With such a configuration, the physician can connect the portable external memory 41 to an external device such as a computer and thereby can copy data of biological sounds recorded in the memory 41 in the computer. As a result, the physician can analyze the biological sounds in more detail with the computer.

The stethoscope apparatus 20 may have, in place of the external memory interface 36, an interface for a USB (Universal Serial Bus). In this case, a USB cable is connected to the stethoscope apparatus, and through the USB interface, data communication is carried out between the stethoscope apparatus and the external device.

FIG. 10 is a partial sectional view showing a stethoscope apparatus involving still another embodiment of the invention. FIG. 11 is a block configuration diagram of the stethoscope apparatus. A diaphragm 6 provided to a diaphragm portion 51 of a stethoscope apparatus 30 is loaded with a contact sensor 24 that detects, for instance, that the stethoscope apparatus 30 came into contact with a patient. The contact sensor 24 is disposed, for instance, at a substantial center of the diaphragm 6. As the contact sensor 24, for instance, an electrostatic sensor or a piezoelectric sensor can be used. As shown in FIG. 11, a power supply controller 35 controls based on a signal detected by the contact sensor 24 a power supply portion 34 so as to input power.

According to such a stethoscope apparatus 30, when a physician brings the stethoscope apparatus 30 into contact with a patient, electric power is inputted; accordingly, power saving can be realized. The stethoscope apparatus 30, being a battery type as mentioned above, is particularly strong in demand for power saving; accordingly, in this case, an advantage is very large. Furthermore, the electric power is not inputted until the contact sensor 24 comes into contact with the patient; accordingly, the stethoscope apparatus does not collect noises before the stethoscope apparatus 30 is brought into contact with the patient. Still furthermore, for the physician, since an operation of pushing a power switch can be omitted, the stethoscope apparatus 30 can be used with a sense as if an existing non-electronic stethoscope apparatus is used.

In the stethoscope apparatus 30, the contact sensor 24 can be disposed to any place thereof as far as it comes into contact with the patient. For instance, an attachment portion of the contact sensor 24 is formed to a housing 11 and the contact sensor 24 may be attached to the attachment portion.

The stethoscope apparatus 30 may have a timer function of the power supply portion 34. For instance, as mentioned above, a signal detected by the contact sensor 24 triggers to input electric power. Thereafter, at a predetermined time after a signal became not to be detected with the contact sensor 24, the power controller 35 can control so that a power supply of the power supply portion 34 may be turned off.

FIG. 12 is a partial sectional view showing a stethoscope apparatus involving further still another embodiment of the invention. As shown in FIG. 12(A), in a stethoscope apparatus 40, an angle adjusting mechanism that connects a diaphragm portion 1 and a speaker portion 2 is constituted of a universal joint 25. In the universal joint 25, a spherical body 25a fixed to a housing 12 of, for instance, the speaker portion 2 is rotatably fitted in a receiving body 25b disposed to the housing 11 of the diaphragm portion 1. According to such a configuration, although a range of angle of the speaker portion 2 to the diaphragm portion 1 is limited, the speaker portion 2, without being restricted in a direction in which it moves, can conveniently move in all directions. For instance, a state shown in FIG. 12(B) is a state where an angle and a direction similar to FIG. 6 are taken. A state shown in FIG. 12(C) is a state where the speaker portion 2 is upside down. Other than the states shown in FIGS. 12(A) through 12(C), for instance, with a posture of the diaphragm portion 1 kept as it is, an output surface of the speaker sound of the speaker portion 2, among FIGS. 12(A) through 12(C), can be made a state that faces toward a front side (a state where the cover 19 shown in FIG. 4 faces a front side in FIG. 12).

The universal joint is not restricted to one that uses the spherical body 25a shown in FIG. 12. For instance, a structure where the diaphragm portion 1 and the speaker portion 2 move in at least two planes is called a universal joint. The structure where the diaphragm portion 1 and the speaker portion 2 move in two planes can be realized with for instance a biaxial hinge mechanism.

FIG. 13 is a perspective view showing a stethoscope apparatus involving another embodiment of the invention. The stethoscope apparatus 50 includes substantially parallelepiped housings 151 and 152, and the housings 151 and 152 are rotatably connected through a hinge mechanism 65. The housing 151 incorporates a not shown speaker body and from a plurality of slits 151a disposed on a surface of the housing 151 sounds are outputted. Holes therefrom the sounds are outputted are not necessarily slit-like ones but may be mesh-like ones or a plurality of round-holes such as shown in FIG. 1. FIG. 14 is a perspective view showing an opposite side of the stethoscope apparatus 50 shown in FIG. 1. The housing 152 is vibratably loaded with a diaphragm 56 as shown in FIG. 14.

FIG. 15 is a side view showing the stethoscope apparatus 50. The housing 151 is provided with a pressure member 54 that plays a function of a clip. Specifically, one end 54a of the pressure member 54, supported by the housing 151, forms a fixed end, and the other end 54b of the pressure member 54 forms a free end. Thereby, the pressure member 54 is imparted with the spring properties and thereby a clip mechanism is realized. So far, since a stethoscope is provided with an auditory tube, when a physician hooks the auditory tube on own neck, without using a hand, the stethoscope can be carried with. The stethoscope apparatus 50 involving the embodiment does not have such an auditory tube and cables. Accordingly, when it has such a clip mechanism, for instance, by clipping the stethoscope apparatus 50 with the pressure member 54 to a pocket of clothing that the physician wears, the physician can conveniently carry the stethoscope apparatus 50. In particular, when the pressure member 54 is formed into a frame-shape so as to fit to a shape of the housing 151, a clipped state can be stabilized.

FIG. 16 is a side view showing a state where the stethoscope apparatus 50 is opened, that is, the housings 151 and 152 are opened. Thus, by use of the hinge mechanism 65, the housings 151 and 152 can be constituted so as to be opened at an angle less than 180° at most or 180° or more. In addition to the hinge mechanism 65, the housings 151 and 152 may be constituted twistably. That is, the housing 151 may be constituted so as to move against the housing 152 in a direction (in a direction deviating from a direction in parallel with the axial direction) where a surface (an output surface of speaker sounds) on which the slit 151a (FIG. 13) is disposed twists to an axial direction (a vertical direction to a page space in FIG. 16) of a rotation axis 65a of the hinge mechanism 65.

FIG. 17 is a block configuration diagram of a stethoscope apparatus involving still another embodiment of the invention. The stethoscope apparatus 60 includes a ROM (Read Only Memory) 37 that stores for instance a predetermined program and database. The ROM may be a semiconductor memory, a memory such as a magnetic disc, or memories other than the above. As shown in FIG. 18, specifically, the ROM 37 stores a pattern-matching program 45, a pathological information output program 46 and a pathological pattern database 47.

The pathological pattern database 47 is a database where all patterns of biological sounds obtained with the stethoscope apparatus 60 (for instance, typical waveform patterns of the biological sounds) are stored in association with pathological information (for instance, a disease name or a symptom due to the disease). The pattern-matching program 45 extracts one or a plurality of pathological patterns most similar to a pattern of a biological sound actually obtained with the microphone 8 from the pathological pattern database 47. The pathological information output program 46 is a program for outputting, with a speaker 9 as sounds, pathological information corresponding to thus extracted pathological pattern. As a method with which the pattern-matching program 45 extracts a pathological pattern, for instance, a frequency of a waveform obtained with the microphone 8, a kind of a continuous sound, a kind of a discontinuous sound, combinations thereof, number of times or frequency of continuous or discontinuous sounds, or sound pressure levels thereof are used. A threshold value for these values is determined to extract. However, other than these, various methods can be considered.

By use of the diagnosis due to the pattern-matching method, a physician, inhibited from misdiagnosing, can effectively diagnose. Furthermore, since the pathologies are notified as sounds from the speaker 9, a patient, being able to acknowledge the pathologies from both of the physician and the stethoscope apparatus 60, can be diagnosed at more ease. In recent years, medical accidents due to physicians are not scarce. It is important to inhibit the physicians from misdiagnosing at an early stage from the time of diagnosis with a stethoscope apparatus, which is an early stage of a medical process.

The invention, without restricting to the embodiments described above, can be variously modified.

In the stethoscope apparatus according to the respective embodiments, an angle of a speaker portion can be controlled by use of a hinge or a universal joint. However, a microphone and a speaker may be mounted in one integral housing that does not have such an angle adjusting mechanism.

Furthermore, the stethoscope apparatus according to the respective embodiments are constituted with a diaphragm; however, the diaphragm is not necessarily required.

The stethoscope apparatus 10 shown in FIG. 1 and so on and other stethoscope apparatus 20, 30 and 40 are not provided with the clip mechanism (pressure member 54) shown in FIG. 13 and so on; however, these may be provided therewith. In this case, the pressure member preferably has a dimension same or smaller than a width of the housing 11 or 12 of the stethoscope apparatus 10 from a viewpoint of design.

In the stethoscope apparatus involving embodiments shown in FIGS. 17 and 18, the speaker outputs the pathological information as sounds. However, when a stethoscope apparatus is provided with, for instance, a liquid crystal, an EL (Electro-Luminescence) or other display, the pathological information may be displayed on the display as characters or images.

At least one of features of the stethoscope apparatus involving the respective embodiments may be combined to constitute a stethoscope apparatus.

BRIEF DESCRIPTION OF THE DRAWINGS

FIG. 12 is a partial sectional view showing a stethoscope apparatus involving a further still another embodiment according to the invention.

Figure 1:
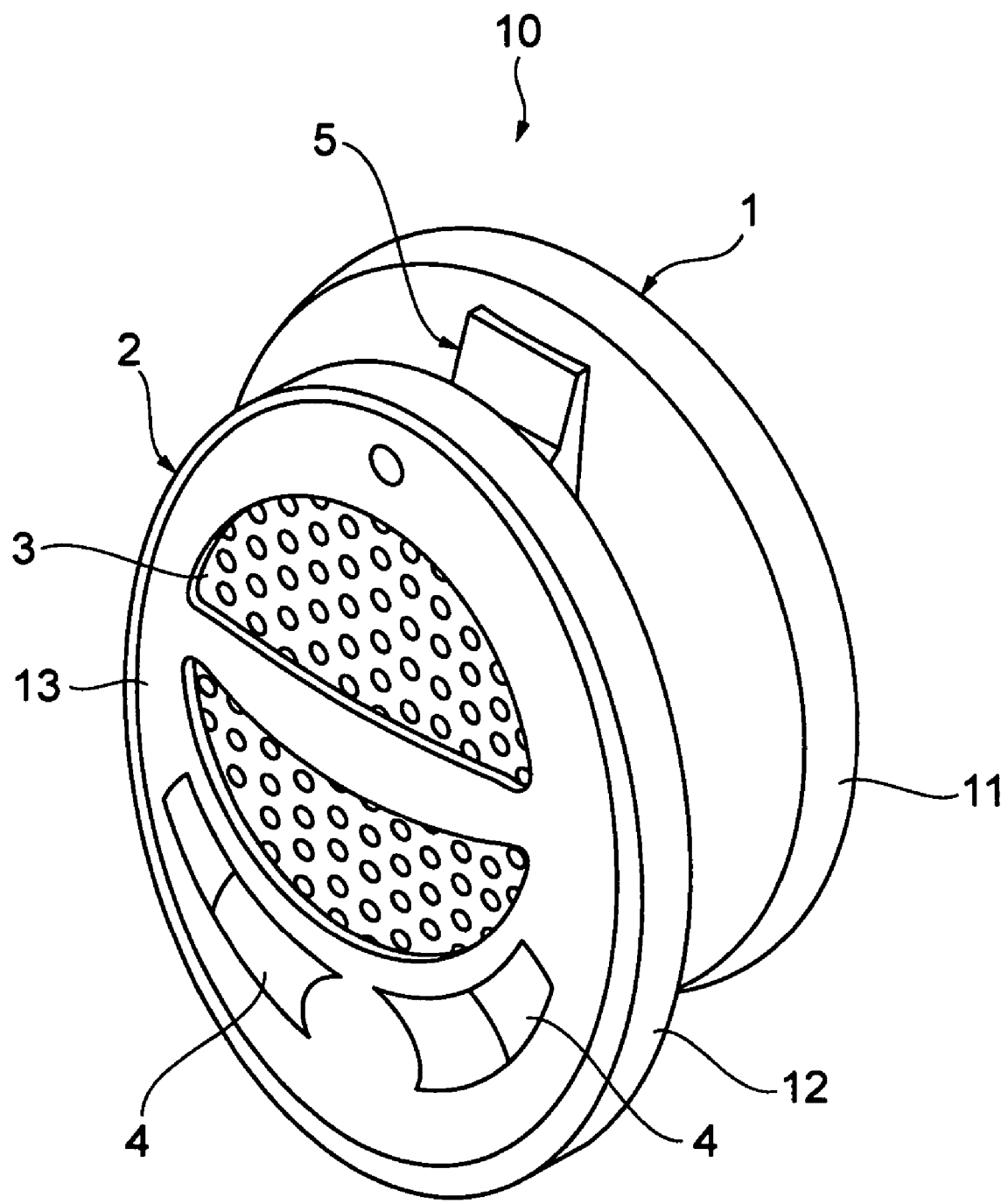
FIG. 1 is a perspective view showing a stethoscope apparatus involving one embodiment according to the invention.
Figure 2:
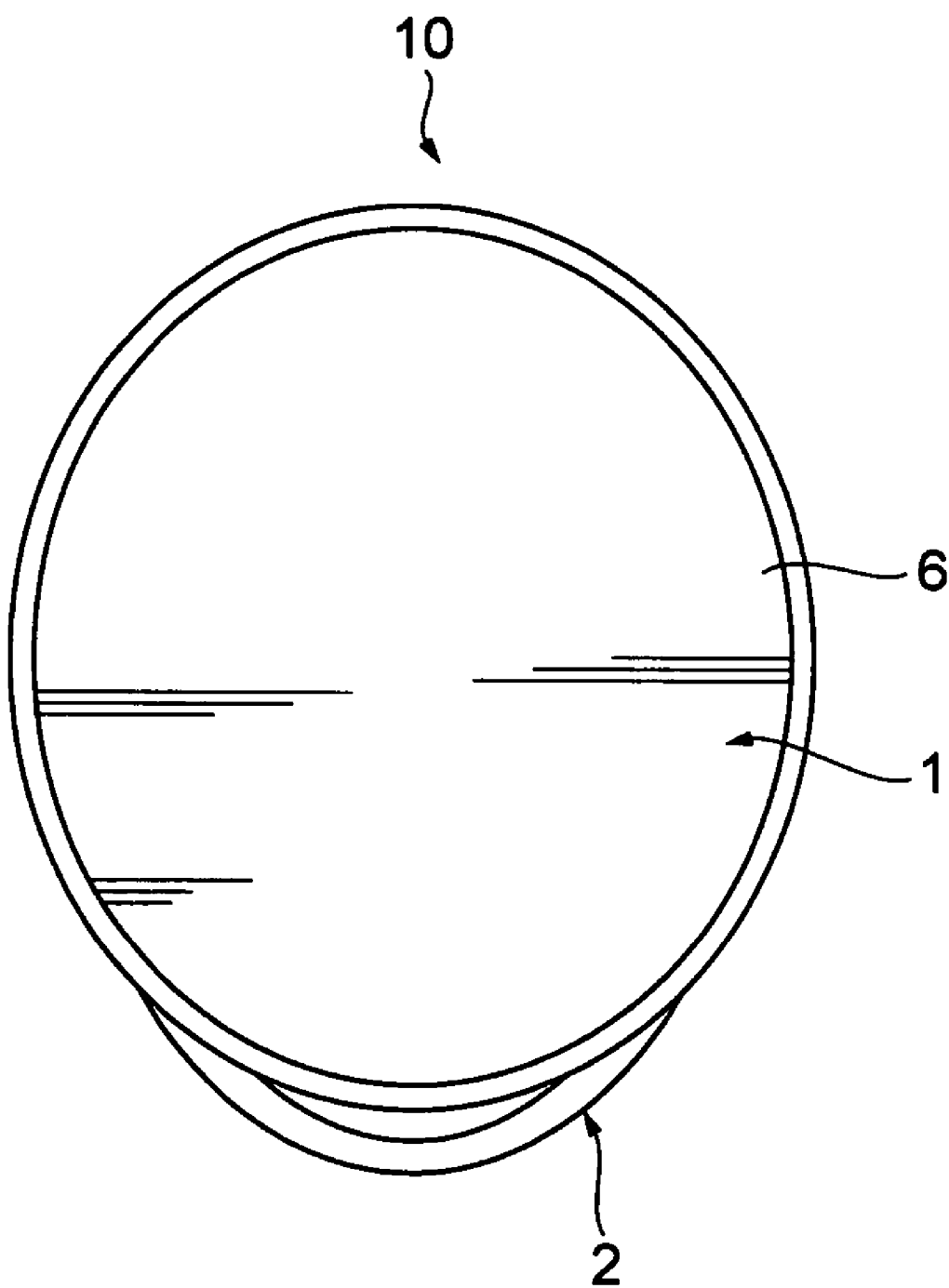
FIG. 2 is a view seen from a diaphragm portion side of the stethoscope apparatus shown in FIG. 1.
Figure 3:
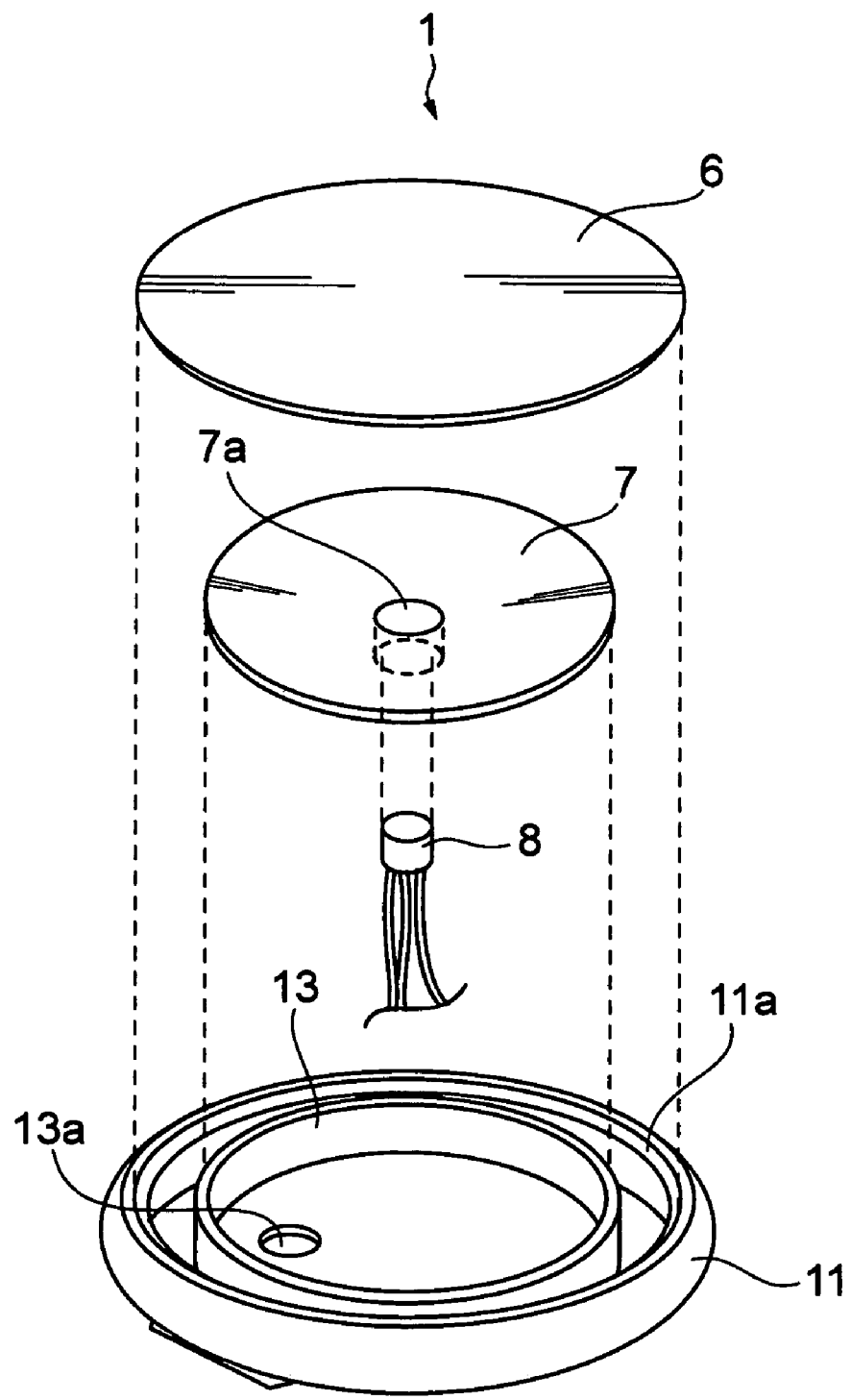
FIG. 3 is an exploded perspective view of the diaphragm shown in FIG. 1.
Figure 4:
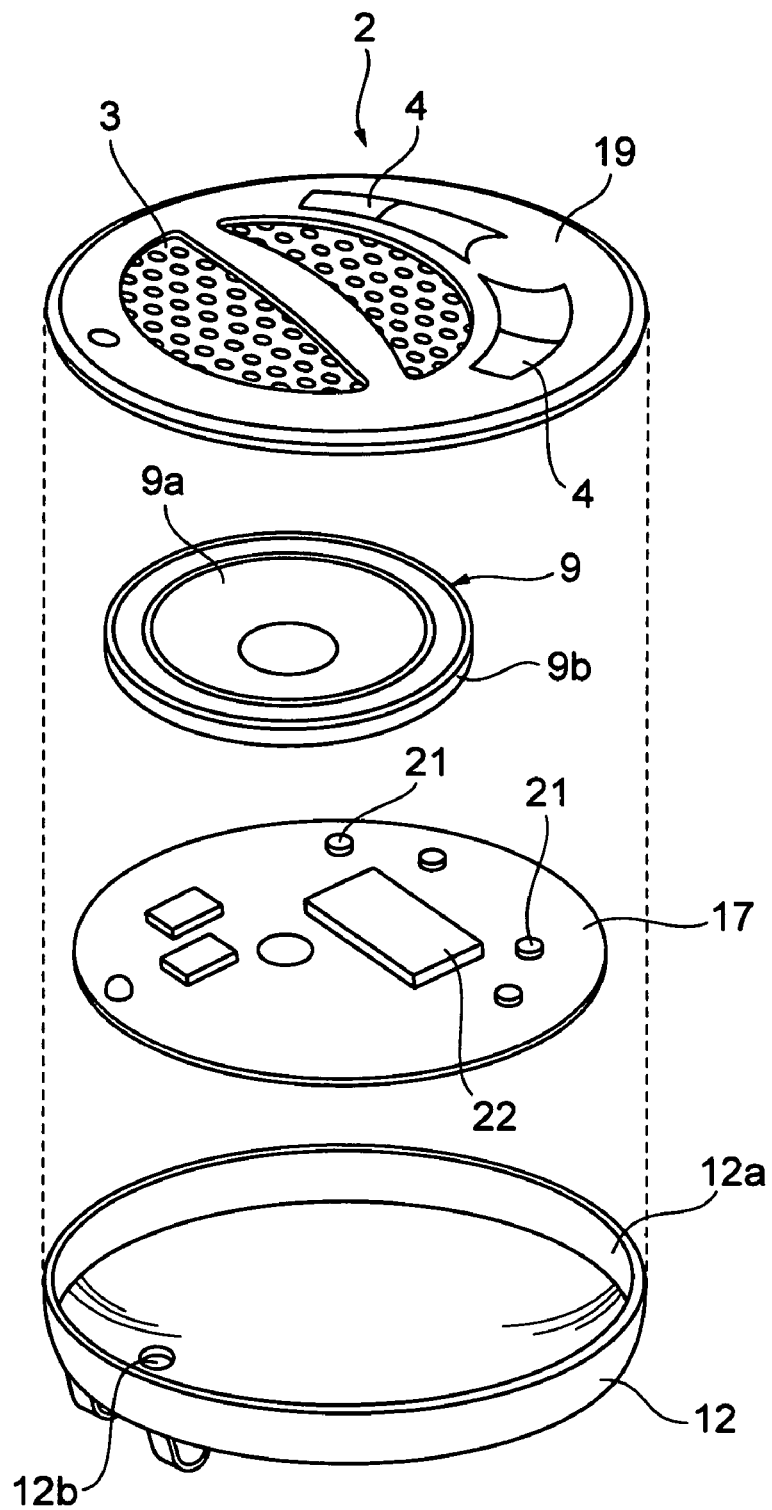
FIG. 4 is an exploded perspective view showing a speaker portion of the stethoscope apparatus.
Figure 5:
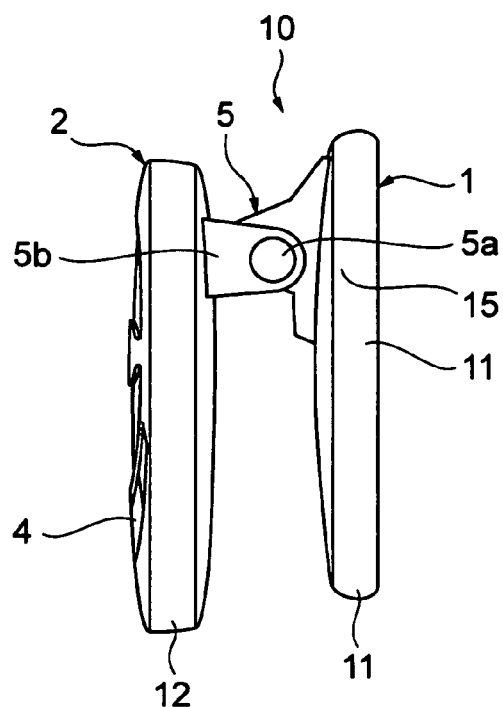
FIG. 5 is a side view of the stethoscope apparatus.
Figure 6:
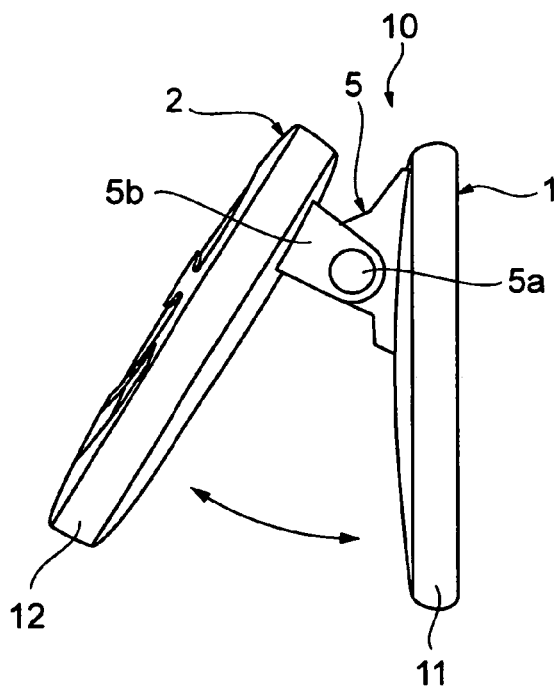
FIG. 6 is a side view showing a state where the stethoscope apparatus is opened with a certain angle.
Figure 7:
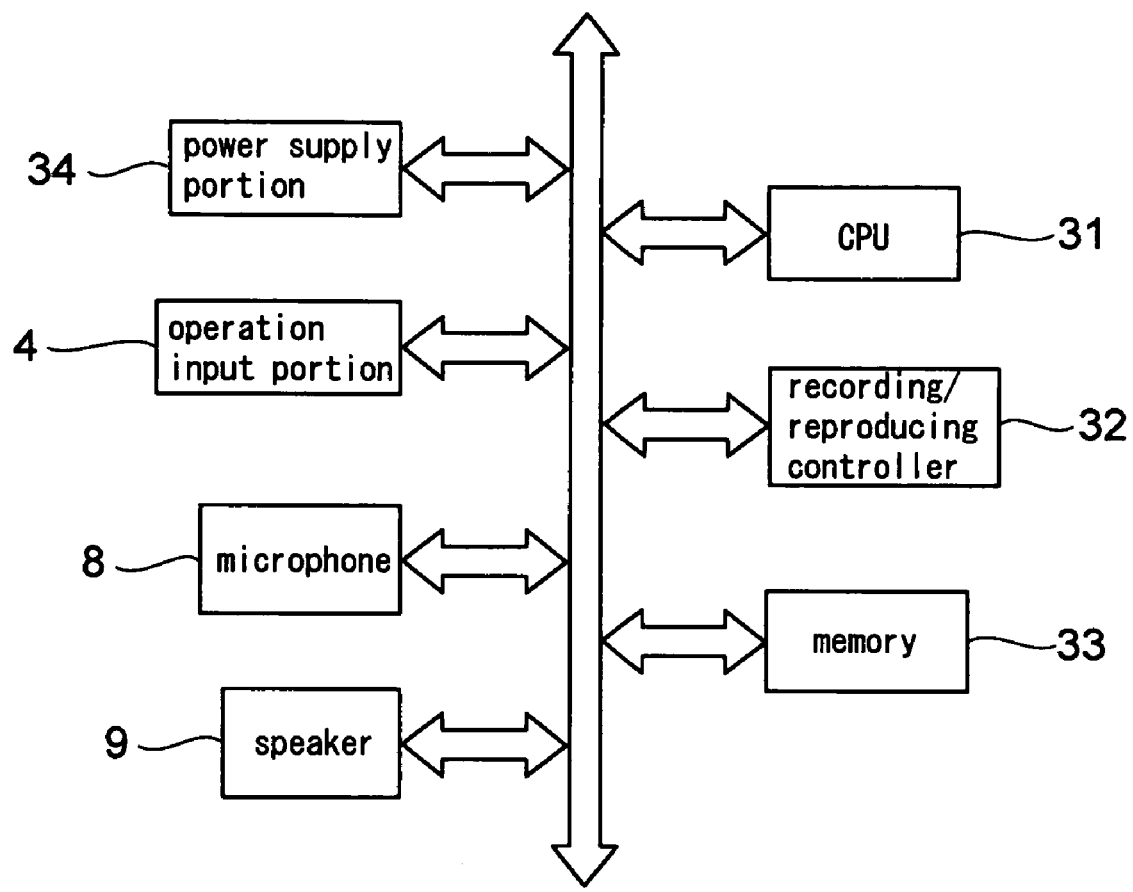
FIG. 7 is a block diagram showing an electrical configuration of the stethoscope apparatus.
Figure 8:
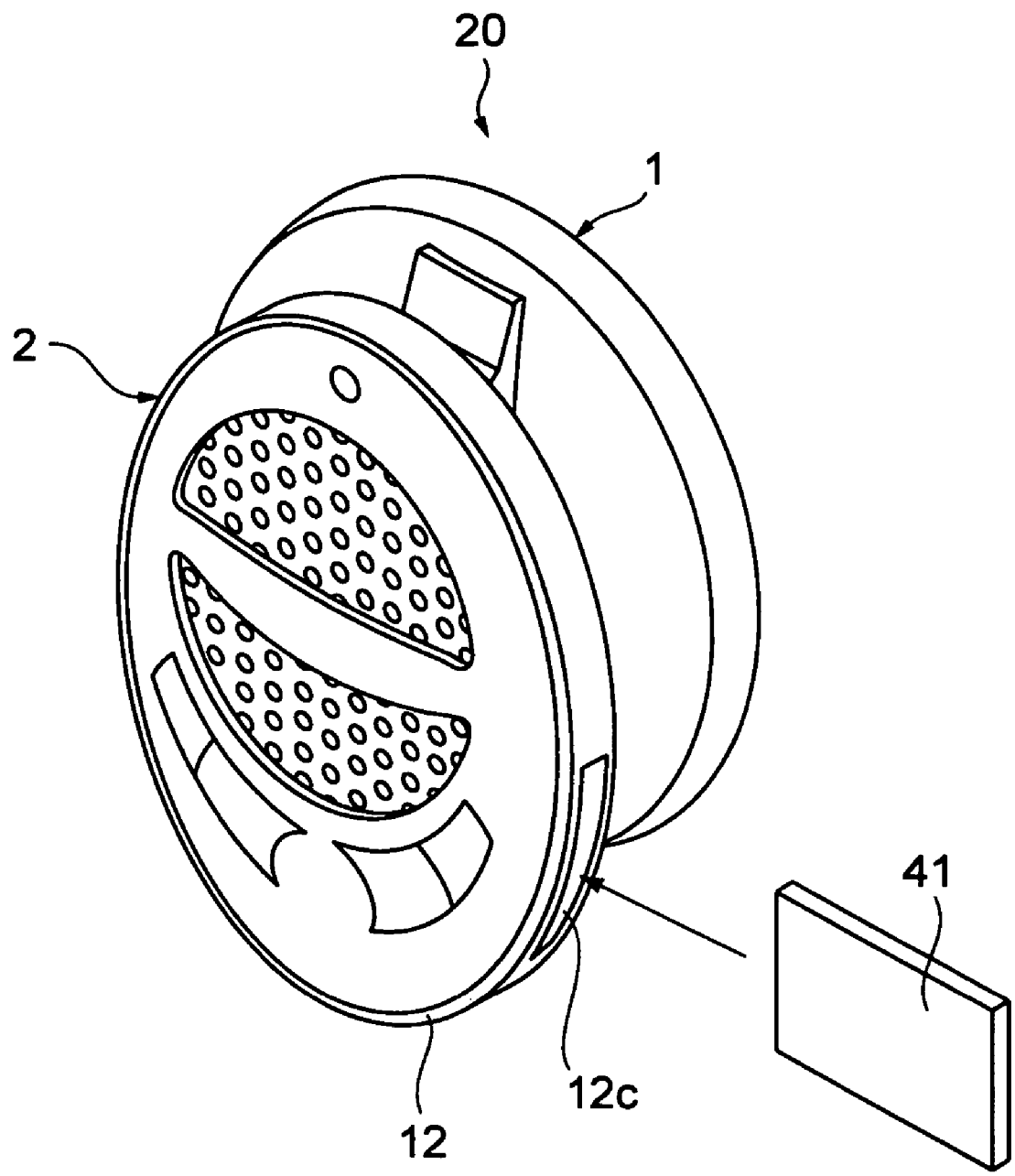
FIG. 8 is a perspective view showing a stethoscope apparatus involving another embodiment according to the invention.
Figure 9:
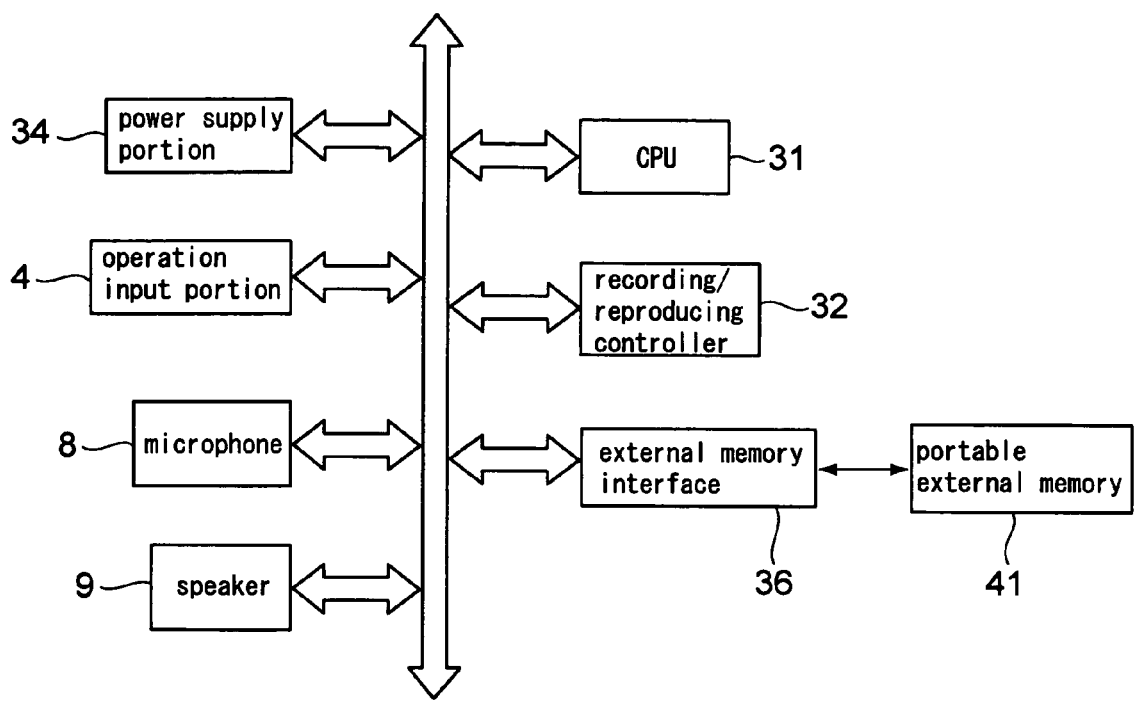
FIG. 9 is a block configuration diagram of the stethoscope apparatus shown in FIG. 8.
Figure 10:
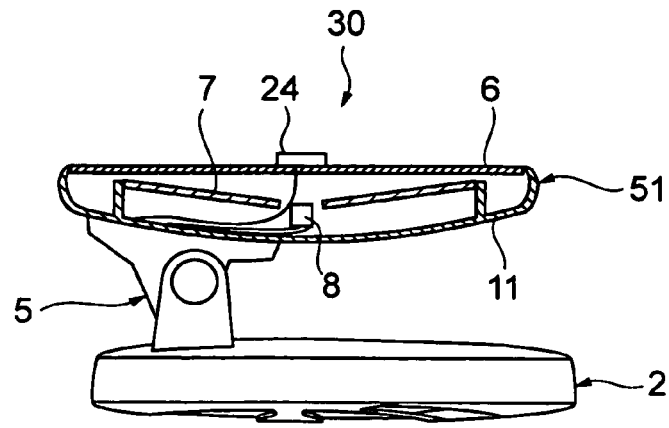
FIG. 10 is a partial sectional view showing a stethoscope apparatus involving a still another embodiment according to the invention.
Figure 11:
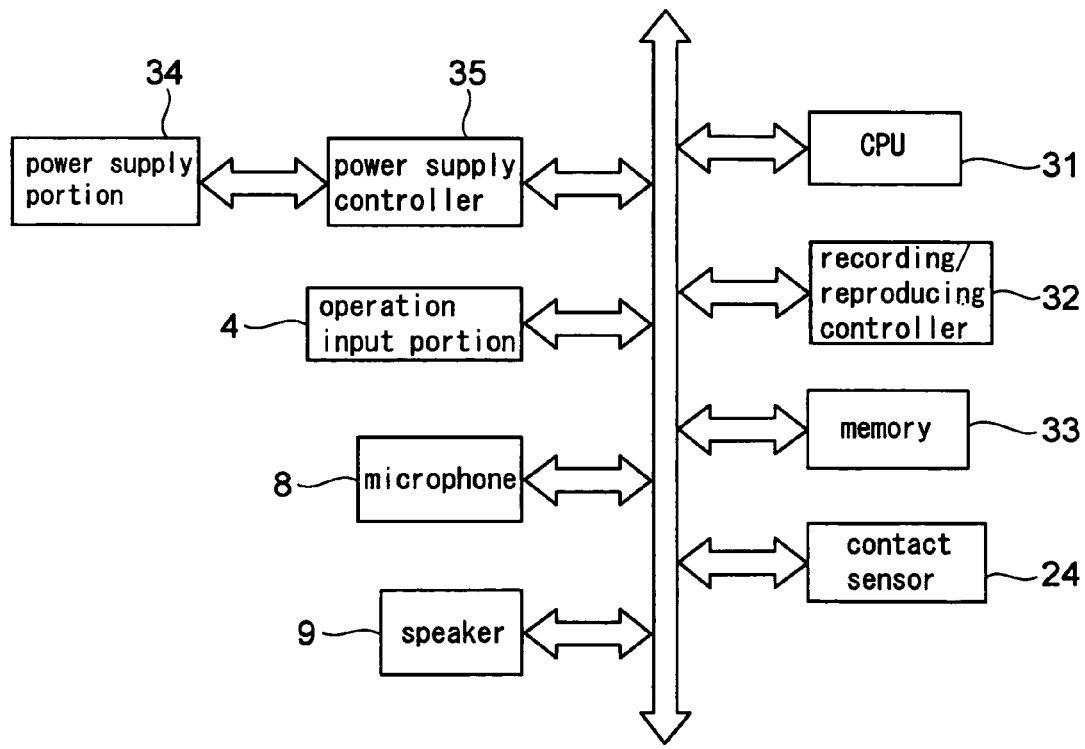
FIG. 11 is a block configuration diagram according to the stethoscope apparatus.
Figure 13:
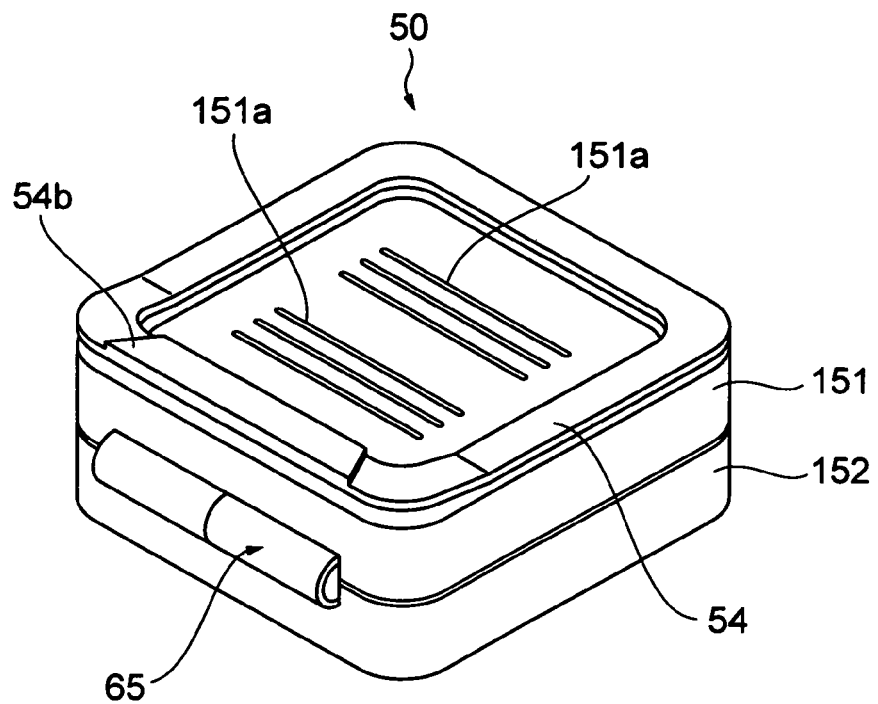
FIG. 13 is a perspective view showing a stethoscope apparatus involving another embodiment according to the invention.
Figure 14:
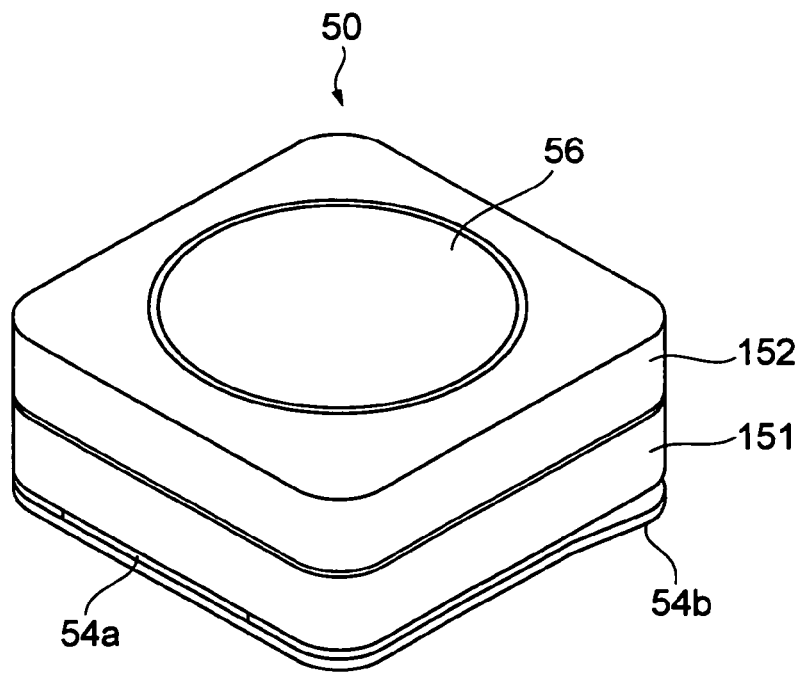
FIG. 14 is a perspective view shown from an opposite side of the stethoscope apparatus shown in FIG. 13.
Figure 15:
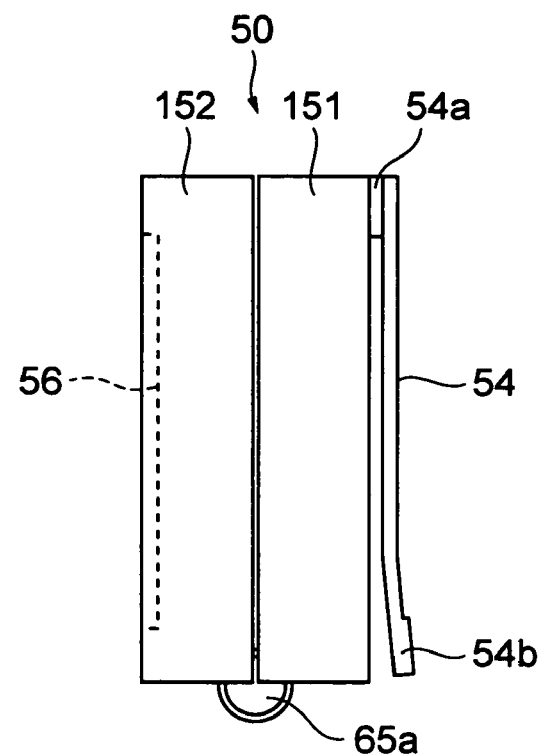
FIG. 15 is a side view showing the stethoscope apparatus shown in FIG. 13.
Figure 16:
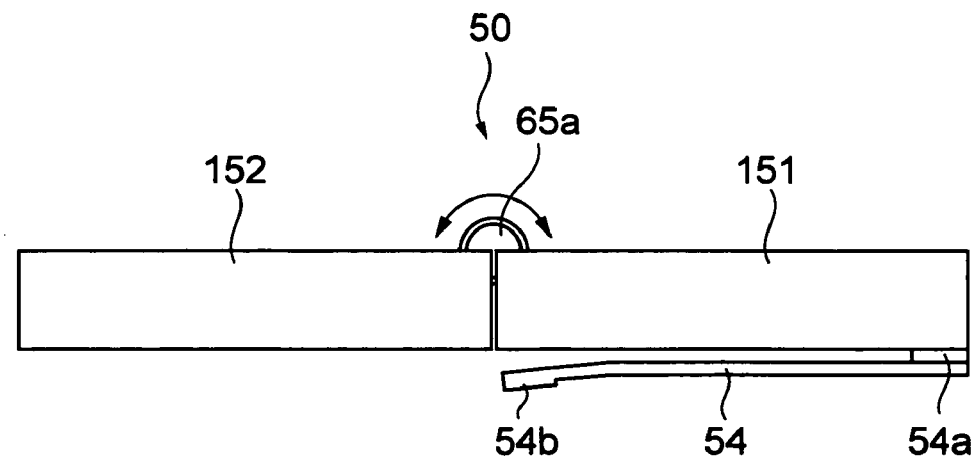
FIG. 16 is a side view showing a state where the stethoscope apparatus shown in FIG. 13 is opened.
Figure 17:
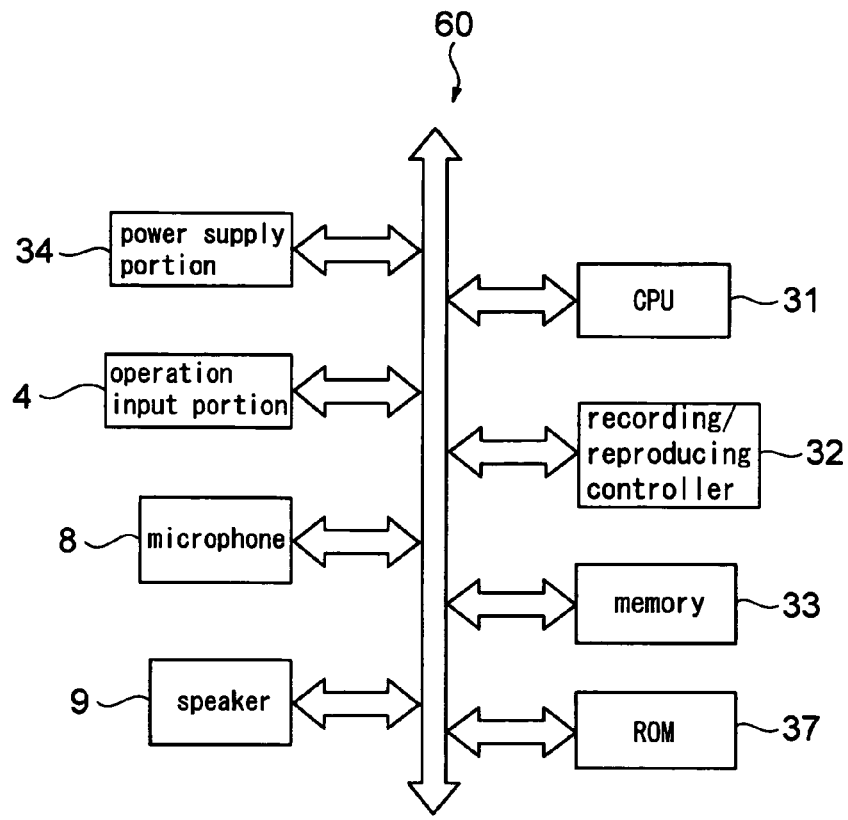
FIG. 17 is a block configuration diagram of a stethoscope apparatus according to still another embodiment of the invention.
Figure 18:
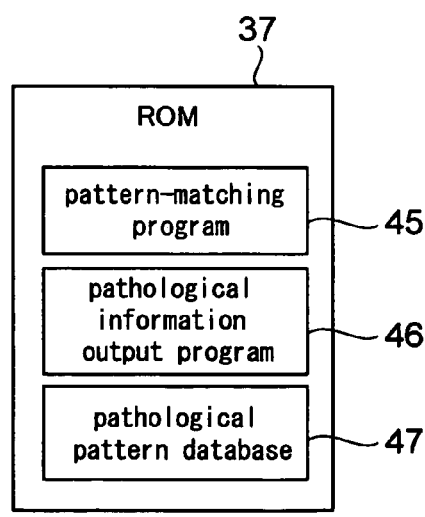
FIG. 18 is a block diagram showing data stored in a ROM shown in FIG. 17.

EXPLANATION OF CODES 1, 51 . . . diaphragm portion
2 . . . speaker portion
5, 65 . . . hinge mechanism
6, 56 . . . diaphragm
8 . . . microphone
9 . . . speaker body
10, 20, 30, 40, 50, 60 . . . stethoscope apparatus
11, 12, 151, 152 . . . housing
12c . . . slot
17 . . . circuit board
24 . . . contact sensor
25 . . . universal joint
31 . . . CPU
32 . . . recording/reproducing controller
33 . . . memory
34 . . . power supply
35 . . . power supply controller
36 . . . external memory interface
37 . . . ROM
41 . . . portable external memory
45 . . . pattern matching program
46 . . . pathology information output program
47 . . . pathology pattern data base

What is claimed is:

1. A tubeless stethoscope apparatus, comprising: a microphone; a speaker that includes a vibrating plate vibrating in accordance with an electrical signal generated by the microphone; a first housing of the tubeless stethoscope on which the microphone is mounted; a second housing of the tubeless stethoscope on which the speaker is mounted; and one of a uniaxial hinge mechanism and a biaxial hinge mechanism for adjusting an angle between the first housing of the tubeless stethoscope and the second housing of the tubeless stethoscope to fix positions of the first housing and the second housing.

2. The tubeless stethoscope apparatus as set forth in claim 1, wherein the first housing has a contact portion that is brought into contact with a patient; and wherein the contact portion and the speaker, respectively, are disposed to the first and second housings so that the speaker outputs the sound to an opposite side of the contact portion when the first and second housings are closed with the hinge mechanism.

3. The tubeless stethoscope apparatus as set forth in claim 1, further comprising: a sensor that is disposed to the first housing and detects that the tubeless stethoscope mechanism has come into contact with a patient; and a power supply portion that inputs electric power in accordance with a signal detected by the sensor.

4. The tubeless stethoscope apparatus as set forth in claim 1, further comprising: a memory portion that memorizes a sound obtained by the microphone; and a memory controller that controls the memory operation.

5. The tubeless stethoscope apparatus as set forth in claim 1, further comprising: an interface provided on the second housing having a slot capable of being loaded with a portable recording medium: the interface is capable of communicating sound data obtained by the microphone to the recording medium when the recording medium loaded in the; and a controller that controls at least one of recording of the data in the recording medium through the interface and reproducing of data recorded in the recording medium through the interface.

6. The tubeless stethoscope apparatus as set forth in claim 1, further comprising: storing means for storing data of patterns of a plurality of biological sounds; and pattern-matching means for pattern-matching a biological sound obtained from a patient with the microphone with the respective pattern data storing with the storing means.

7. The tubeless stethoscope apparatus as set forth in claim 1, wherein the storing means store a plurality of informations on pathology so that each of the information corresponds to the respective pattern data; and the tubeless stethoscope apparatus further comprises: pathology output means for outputting the information of the pathology corresponding to at least one pattern data matched by the pattern-matching means is extracted from the storing means and outputted through the speaker.

8. The tubeless stethoscope apparatus as set forth in claim 1, wherein the storing means store a plurality of informations on pathology so that each of the information corresponds to the respective pattern data; and the tubeless stethoscope apparatus further comprising: display means; and display control means that control so that information of the pathology corresponding to at least one pattern data matched by the pattern matching means is extracted from the storing means and displayed through the display means.

* * * * *